United States Patent [19]

Comben et al.

[11] Patent Number: 4,874,371
[45] Date of Patent: Oct. 17, 1989

[54] CONTROL HANDLE

[75] Inventors: Richard H. Comben, Minneapolis; Byron L. Gilman, Plymouth; Leonid Shturman, Minnetonka, all of Minn.

[73] Assignee: Medilase, Inc., Minneapolis, Minn.

[21] Appl. No.: 117,479

[22] Filed: Nov. 5, 1987

[51] Int. Cl.$^4$ ................................................ A61B 1/00
[52] U.S. Cl. .......................................... 604/95; 128/4; 128/6
[58] Field of Search ........................... 604/95; 128/4, 6

[56] References Cited

U.S. PATENT DOCUMENTS

| 3,470,876 | 10/1969 | Barchilon . |
| 3,547,103 | 12/1970 | Cook . |
| 3,631,848 | 1/1972 | Muller . |
| 4,277,168 | 7/1981 | Oku ..................................... 128 4 X/ |
| 4,405,314 | 9/1983 | Cope . |
| 4,418,688 | 12/1983 | Loeb . |
| 4,517,974 | 5/1985 | Tanner . |
| 4,617,915 | 10/1986 | Arakawa .................................... 128/4 |
| 4,646,742 | 5/1987 | Packard et al. . |
| 4,648,892 | 3/1987 | Kittrell et al. . |
| 4,662,368 | 5/1987 | Hussein et al. . |
| 4,664,113 | 5/1987 | Frisbie et al. . |
| 4,669,465 | 6/1987 | Moore et al. . |
| 4,740,195 | 4/1988 | Lanciano .......................... 604/95 X |

FOREIGN PATENT DOCUMENTS 2175505A 12/1986 United Kingdom .

OTHER PUBLICATIONS

Steerable Fiber Optic Catheter Delivery of Lase Energy in Atherosclerotic Rabbits, *AM. Heart J. 111.1065, 5/1986.*

Primary Examiner—Allen M. Ostrager
Attorney, Agent, or Firm—Vidas & Arrett

[57] ABSTRACT

A control handle for use in rotating a catheter and for rotating a working means at the end of the catheter.

22 Claims, 3 Drawing Sheets

CONTROL HANDLE

FIELD OF THE INVENTION

This invention relates to a control handle which rotates a catheter and/or a working means at the end of the catheter by means of an elongated torque means. Although particularly described with reference to laser angioplasty, the invention has broad applicability to various medical instruments such as endoscopes, angioscopes, catheters, microcatheters, and the like.

BACKGROUND OF THE INVENTION

This invention relates in general to controlling the positioning and/or aiming of medical instruments such as endoscopes, angioscopes, catheters, microcatheters and other medical instruments. It specifically relates to a device for controlling the positioning of a laser for performing laser surgery e.g., angioplasty and treatment of atherosclerosis and the like.

The control handle disclosed is preferably used to operate a device such as that described in copending application Ser. No. 066,937 entitled Laser Angioplasty, filed June 25, 1987 and incorporated herein by reference. That application discloses a device for aiming light transmitting fibers, fiber bundles or other working means in a catheter system used in laser surgery. However, the control handle of the subject invention may be used to position and aim many other medical devices as well. For purposes of this application a catheter is defined generally as any device which is inserted into the body and is operated at its distal end by remote control at its proximal end.

In particular this invention relates to the precise positioning of optical fiber bundles for imaging as well as the aiming of laser radiation transmitting fibers which are controlled at the distal end of a catheter by means of an elongate torque transmitting element e.g., a torque wire, a torque tube, a torque matrix or composite element or the like and a control handle.

Precise aiming of the laser energy is extremely important in angioplasty to avoid damage to the vessels. The control handle of the subject invention aids in such aiming by providing control for positioning the working means contained at the distal end of the catheter. In using the handle one step in aiming is accomplished by rotating the entire control handle, thereby rotating the entire catheter. A second step in aiming is achieved by rotating the elongate torque transmitting means e.g., a torque wire, torque tube or equivalent, which in turn rotates the working means at the distal end of the catheter.

SUMMARY OF THE INVENTION

In its most preferred form the invention comprises a fiber optic catheter suitable for performing medical procedures in a vascular lumen or other cavity within a patient. The catheter has a distal end to be inserted into a patient and a proximal end, including a control handle held by a physician for directing and controlling the contemplated treatment procedure. More specifically, the catheter includes an elongated external tube containing a laser light transmitting means, such as an optical fiber. The catheter may also contain one or more fiber optic viewing bundles and accessory lumens, etc.

As specifically disclosed, the invention comprises a control handle which allows a physician to turn a control wheel and thereby rotate a working means at the distal end of the catheter. The control wheel is provided with tactile feedback to inform the physician of various degrees of rotation, such as each 45 degree of rotation, of the control wheel. The wheel rotates a torque wire or equivalent which in turn rotates the working means at the distal end of the catheter. The control wheel preferably has eight tactile ridges spaced 45 degrees around the circumference of the control wheel. The control handle also has an opening in which the control wheel is positioned and which allows the physician to rotate the control wheel in steps of two tactile ridges in either direction whereby the physician is able to determine by feel that the working means has been rotated 90 degrees. The control wheel may be provided with a variety of other tactile surfaces to accomplish the same tactile feedback mechanism. The control wheel may also be provided with a different number of ridges to provide degrees of rotation in increments or steps other than 45 degrees, such as 30 or 60 degrees, or any other desired amount.

In a laser angioplasty device the rotatable working means at the distal end of the catheter will typically be an optical fiber and/or bundle which is aimed so as to direct the fiber or bundle toward a particular site within a vascular lumen. The aiming means comprises a rotatable positioning support body carried at the distal end of the catheter. The positioning body is preferably located in a position displaced with respect to the longitudinal axis (first axis) of the catheter device (as described in the aforementioned copending application) such that rotation of the catheter device about its longitudinal axis causes rotation of the positioning body about the longitudinal axis (first axis) of the catheter device. The rotation of the entire catheter about its longitudinal axis (first axis) describes a first positioning or aiming mode. The optical fiber or other workpiece is received and held by the positioning support body in a location displaced relative to the positioning support body's axis of rotation (second axis) such that rotation of the positioning support body rotates the optical fiber or other workpiece about the center of rotation of the positioning body. The rotation of the positioning body by means of the torque wire or other elongated torque transmitting means described a second positioning or aiming mode. The combined rotational movements of the positioning support body per se and the catheter device per se enables the physician to position and aim the optical fiber or other work piece at the distal end of the catheter at any selected cross-sectional point in a vascular lumen or other cavity of a patient, as desired.

As already noted, in other embodiments, the positioning support body may carry both an imaging fiber bundle and a lasing optical fiber or one or the other alone or other workpieces. Also, the rotatable positioning support body may extend along and even beyond the entire length of the catheter device or may take the form of a relatively shortened body located only in the distal end portion of the catheter. In addition, it is within the contemplation of the invention to provide more than one elongate torque transmitting means such as a torque wire or equivalent and corresponding operating means to allow for the more precise control of the aiming of various working means located at the distal end of the catheter.

BRIEF DESCRIPTION OF THE DRAWINGS

FIG. 5 is a pictorial exploded view of the handle shown in FIG. 1;

FIG. 6 is an enlarged detail of the control wheel with parts cut away;

FIG. 7 is an alternative embodiment of the control wheel enclosure element;

DESCRIPTION OF THE PREFERRED EMBODIMENT

Figure 1:
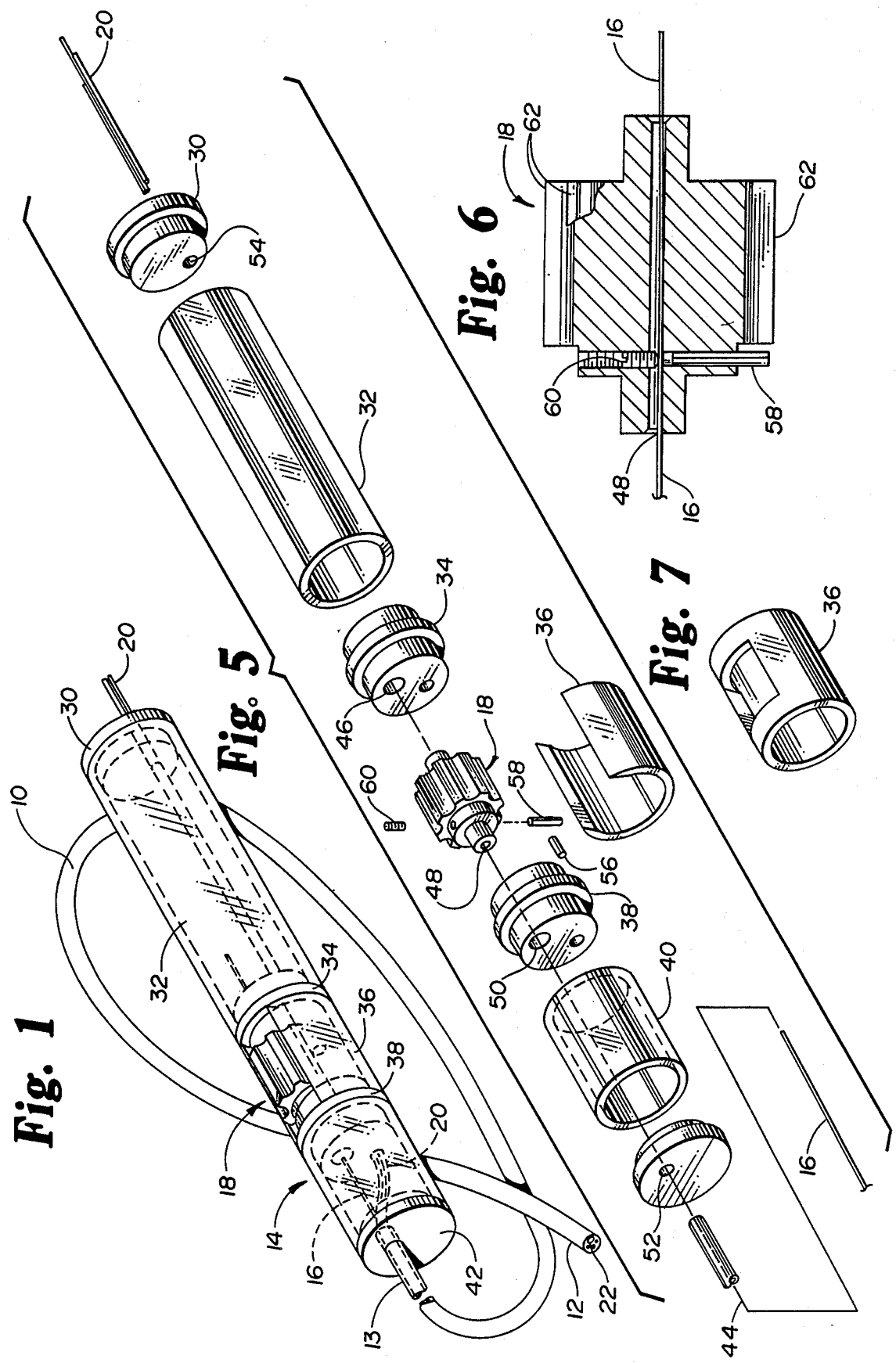
FIG. 1 is an perspective view of a control handle of the invention attached to a laser catheter.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

The present invention in preferred general form comprises a medical device for rotating any type of workpiece located at the end of a catheter-like instrument by remote control means. It is specifically described with reference to a medical device for delivering and applying laser radiation to a site in a vessel lumen of a patient. The radiation can be used to vaporize atherosclerotic plaque as disclosed in aforementioned co-pending application Ser. No. 066,937 entitled Laser Angioplasty. Such instruments often times take the form of microcatheters of extremely small diameter. Such instruments are usually readily available in various diameter sizes to suit the particular work site in the lumen in which they are to be located. Thus a physician will have a number of various sized catheters at his disposal during any given procedure and the interchangeability of the catheter with the control handle is desirable.

Referring now to FIGS. 1-7 of the drawing, the catheter device of the present invention in one embodiment comprises any elongated catheter, generally designated 10, having a working distal end generally designated 12. The device is adapted to be inserted into a patient and includes at its proximal end 13 a control handle, generally designated 14, for manipulation and control by a physician as described further hereinbelow. Catheter 10 is generally flexible and comprised of a extruded solid plastic body. Catheter 10 may consist of a single, soft, solid extruded plastic materil or it may consist of a plastic composite reinforced with plastic or metal filaments, such as Dacron ® polyester fiber or stainless steel. Typical plastics such as polytetrafluoroethylene, polyesters, polyethylene polyurethane and silicone may be used. A torque wire 16 extends through catheter 10. Although described here as a torque wire, a torque tube, matrix or composite body or the like is also within the contemplation of the invention. Torque wire 16 is attached at its proximal end to a control wheel (best seen in FIG. 6) generally designated 18, so as to be rotatable therewith. A laser transmitting optical fiber along with an optical fiber bundle or optical fiber means is shown generally at 20 and extends the length of catheter 10 and terminates at the distal end 12 of the catheter and is attached to rotatable positioning support means 22. It is to be understood that a plurality of separate control wheels each with its own torque wire and separately controlled working means or workpiece at the distal end of the catheter is within the scope of the invention.

When the entire control handle 14 is rotated the entire catheter 10 rotates around its longitudinal axis whereby positioning support means 22 is rotatd around the longitudinal axis (first axis) of the catheter. This allows a first means of positioning or aiming of the imaging optical bundle and the laser radiation delivery optical fiber 20. Control wheel 18 is adapted and arranged to rotate torque wire 16 and in turn rotate positioning support means 22 around its own axis (second axis) for a second means positioning or aiming of the optical bundle and the laser radiation delivery optical fiber 20.

Figure 2:
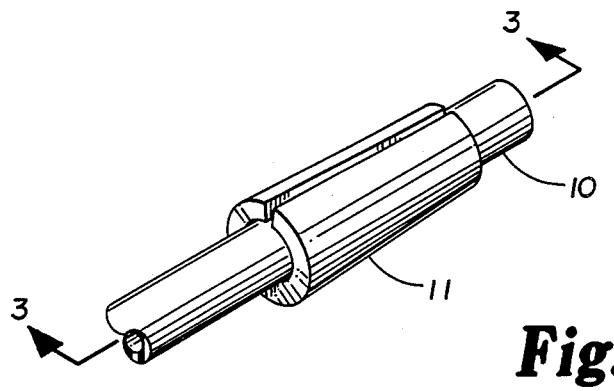
FIG. 2 is an enlarged fragmentary pictorial view of a catheter to handle fitting mechanism.
Figure 3:
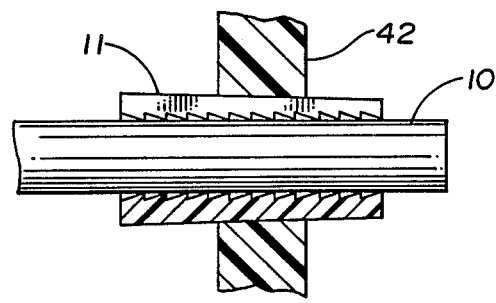
FIG. 3 is a fragmentary sectional detail with parts added taken along line 3—3 in FIG. 2.
Figure 4:
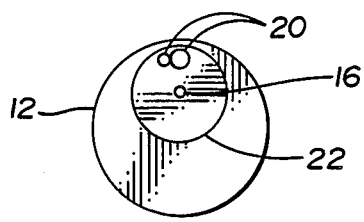
FIG. 4 is an enlarged detail of the distal end of the catheter.

Referring now specifically to FIGS. 2 and 3, the preferred mechanism by which catheter 10 is attached to the control handle 14 is shown. Catheter 10 is provided with a slit handle catheter interlock collar 11. It is of a tapered configuration as shown and is pressure fit into opening 52 of end cap 42. Since collar 11 is carried by catheter 10, when it is closed down by being force fitted into opening 52 it locks catheter 10 to handle 14. Collar 11 may be made of metal or plastic. It is to be understood that a variety of other methods common in the art may be used to secure the control handle to catheter 10.

Referring more specifically now to FIG. 5, an exploded view of FIG. 1 and the control handle is shown. Control handle 14 consists of grip portion 32 having a front and rear end. Portion 32 may be tubular as shown or may have a variety of shapes. Rear end cap 30 is attached to the rear end of tubular grip 32. Rear end cap 30 contains an opening 54 through which the laser fiber and/or optical bundles 20 or the accessories may extend. Rear control wheel support 34 is attached to the front end of tubular grip 32. A control wheel enclosure element 36 is carried between a control wheel support front 38 and rear control wheel support 34. FIG. 7 shows an alternative embodiment of the control wheel envelope 36 although many other embodiments are possible. A front tubular piece 40 (referring again to FIG. 5) is attached to the forward end of front control wheel support 38. Front end cap 42 is attached to the forward end of tubular piece 40. Opening 52 of front end cap 42, opening 50 in front control wheel support 38, opening 48 in control wheel 18 and opening 46 in rear control wheel support 34 are preferably aligned with axis (second axis) 44 along which torque wire 16 extends. Stop 56 (also shown in FIG. 8) is mounted in front control wheel support 38 and so positioned as to cooperate in conjunction with pin 58 (also shown in FIG. 8) in control wheel 18 to limit the rotation of control wheel 18 as described further hereinbelow. Set screw 60 (best seen in FIG. 6 and FIG. 8) is used to clamp torque wire 16 to control wheel 18 for rotation therewith.

Figure 8:
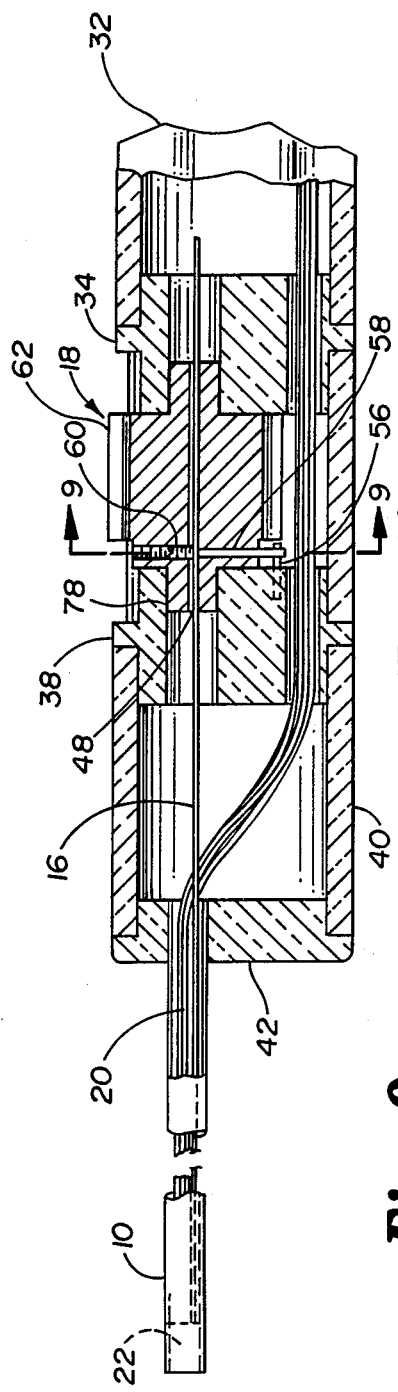
FIG. 8 is a fragmentary view of the handle of FIG. 1 with parts broken away.

Referring now to FIG. 8, this Figure best shows how control wheel 18 is supported for rotation in the control handle. Control wheel 18 has a front axle end 78 and a rear axle end 80 which are mounted in openings 50 and 46 respectively of the front and rear control wheel supports 38 and 34, whereby control wheel 18 is pivotally mounted.

Figure 9:
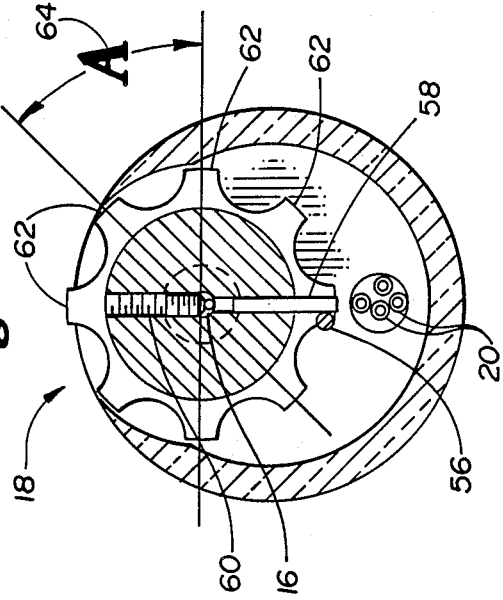
FIG. 9 is a sectional elevation taken along line 9—9 of FIG. 8 and slightly enlarged.

Referring now to FIGS. 8 and 9 together, a cross-sectional view of the control handle along section 9-9 of FIG. 8 is shown in FIG. 9. Torque wire 16 extends directly out of the plane of the drawing through the center of control wheel 18 in FIG. 9. Stop 56 can be seen abutting pin 58 to limit the rotation of control wheel 18. Pin 58 may be made of metal or rubber, the latter allowing it to be overridden. As can be seen best in FIG. 9 control wheel 18 is preferably provided with eight spaced tactile ridge 62 which are positioned 45 degrees apart equally spaced around the circumference of control wheel 18, where angle A, shown at 64, represents 45 degrees. A different number of ridges may be provided to allow other angles corresponding to angles of rotation of the control wheel, as desired. The angle measured from torque wire 16 directly up to the sides of the opening contained in control wheel envelope 36 is 90 degrees as indicated by angle B. Tactile ridges 62 extend above the circumference or outer surface of control wheel enclosure 36 to provide for easy finger contact and manipulation by the physician. Therefore, the physician in rotating the control wheel by two tactile ridges in either direction can tell by feel that the torque wire has been rotated 90 degrees. In moving one tactile ridge in either direction the physician can verify by feel that the torque wire has been rotated 45 degrees.

Figure 11:
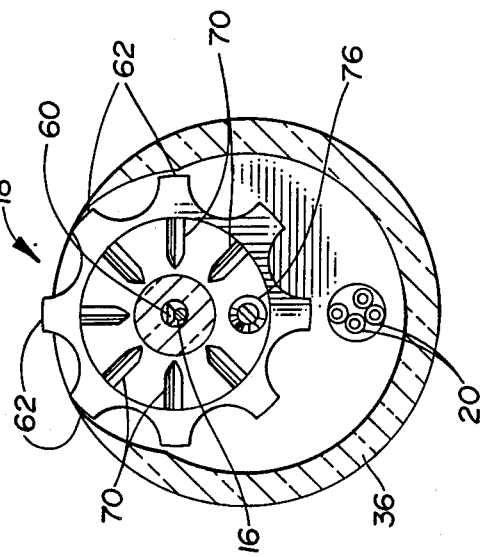
FIG. 11 is a sectional elevation taken along line 11—11 of FIG. 10.
Figure 10:
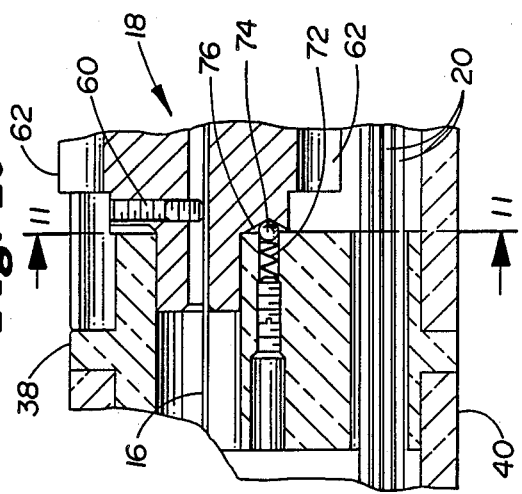
FIG. 10 is a slightly enlarged fragmentary view showing an alternate embodiment of the invention.

Referring now to FIGS. 10 and 11, an alternate embodiment is shown in which additional tactile feed back is provided to the physician when the control wheel is rotated each 45 degree step. This is accomplished by providing a set of correspondingly spaced detentes 70 in the surface of control wheel 18 to work in combination with a spring biased detente ball 74 and compression spring 72 carried by spring detente set screw 86. Each detente 70 shown in FIG. 11 corresponds to a tactile ridge 62 such that any tactile feedback provided by a detente 70 corresponds directly to the ridge correspondingly positioned above it. Thus, each time the physician rotates the control wheel 45 degrees a "click feel" is transmitted via the compression spring 72, detente ball 74 and a detente 70. A relatively deep detente 76 is also provided so that the physician knows when he has rotated the control wheel a total of 180 degrees from a predetermine neutral position. However, providing additional pressure on control wheel 18 allows the physician to override all of the detents shown at 70 and 76. A much stronger click feel is felt by the physician when detente 76 is engaged. In practice the control wheel is initially adjusted to a neutral position such that the wheel may be rotated 180 degrees in either direction. The corresponding "neutral" tactile ridges may be suitably marked or shaped to give an indicator that it is "neutral" in position.

This completes the description of the preferred and alternate embodiments of the invention. Those skilled in the art may recognize other equivalents to the specific embodiment described herein which equivalents are intended to be encompassed by the claims attached hereto.

What is claimed is:

1. A control handle comprising:

a body having a longitudinal axis;
a rotatable control wheel having a center axis about which the wheel is attached to the body;
elongated torque transmitting means extending through the body along an axis coincident with the center axis of the control wheel, off-axis from the longitudinal axis of said body and attached to the control wheel such that rotating the control wheel in a direction substantially perpendicular to the axis rotates the torque means about said center axis over its entire length; and
working means remote from the body attached to the torque means for rotation therewith.

2. The control handle of claim 1, wherein the control wheel includes a set of tactile surfaces spaced a predetermined number of degrees apart around the circumference of the control wheel, whereby the number of degrees between surface is determined by the number of tactile surfaces.

3. The control handle of claim 2 further including a stop attached to the body and a pin attached to the control wheel, the stop and the pin being constructed and arranged to allow less than 180 degrees of rotation of the control wheel in either direction from a predetermined neutral point.

4. The control handle of claim 3, wherein the working means attached to the torque means is an optical fiber means.

5. A control handle for use with a laser catheter comprising:

a grip element adpated to be hand held;
a rotatable control wheel attached to the grip element;
elongate torque transmitting means attached to the control wheel such that rotating the control wheel rotates the torque transmitting means;
a rotatable positioning support means attached to the torque transmitting means at the distal end of the catheter; and
working means remote from the grip element attached to the rotatable positioning support means for rotation therewith.

6. Th control handle of claim 5 wherein the control wheel includes a set of eight tactile ridges spaced 45 degrees apart around the circumference of the control wheel.

7. The control handle of claim 6 further including a stop pin attached to the grip and a pin attached to the control wheel, the stop and the pin being constructed and arranged for mutual abutment whereby less than 180 degrees of rotation of the control wheel in either direction from a predetermined neutral point is permitted.

8. The control handle or claim 7 wherein the working means attached to the positioning support means is an optical fiber means.

9. The control handle of claim 5 further including a handle-catheter interlock collar carried by the catheter and constructed and arranged to be removably received into an opening in an end of the grip.

10. A control handle comprising:

a body having an end portion and at least one passage through the end portion, the body defining a first longitudinal axis and the passage defining a second longitudinal axis parallel with the first axis such that as the body is rotated about the first axis the second axis rotates around the first axis;

a rotatable control wheel defining a longitudinal axis and attached to the body such that at least a portion protrudes from the body and oriented such that the axis of the control wheel is coincident with the second axis;

elongated torque transmitting means having proximal and distal ends and extending coincident with the second axis through the passage and attached to the control wheel at a portion near the proximal end such that rotating the control wheel rotates the torque transmitting means over its entire length;

rotatable positioning support means attached to the torque transmitting means at the distal end thereof; and working means remote from the body attached to the positioning support means for rotation therewith.

11. The control handle of claim 10 wherein the control wheel includes a set of eight tactile ridges spaced 45 degrees apart around the circumference of the control wheel.

12. The control handle of claim 11 further including a stop means attached to the body and a pin attached to the control wheel, the stop means and the pin being constructed and arranged for mutual abutment whereby less than 180 degrees of rotation of the control wheel in either direction from a predetermined neutral point is permitted.

13. The control handle of claim 12 wherein the ridges are each provided with a correspondingly positioned detente which cooperates with the stop, wherein the stop means is spring mounted to provide a tactile feedback for each 45 degrees of rotation of the control wheel.

14. The control handle of claim 13 wherein the detente corresponding to the neutral position is overrideably constructed and arranged to provide a stronger tactile feedback to signify rotation of the control wheel substantially 180 degrees in either direction.

15. The control handle of claim 10 wherein the means attached to the positioning means is an optical fiber means.

16. The control handle of claim 10 further including a handle catheter interlock collar carried by the control handle and constructed and arranged to be removably received into an opening in an end cap of the body.

17. A control handle comprising:
a hand grip body including an opening and having an end portion and at least one passage through the end portion, the body defining a first longitudinal axis and the passage defining a second longitudinal axis parallel with the first axis such that as the body is rotated about the first axis the second axis rotates around the first axis, wherein the opening extends over a 90 degree arc of the circumference of the body relative to the second longitudinal axis;

a rotatable control wheel defining a longitudinal axis and carried by the body such that at least a portion protrudes from the body and oriented such that the axis of the control wheel is coincident with the second axis, the control wheel having a set of eight tactile ridges spaced 45 degrees from each other around the circumference of the control wheel and extending in the control wheel axis direction, the control wheel having a set screw and a pin;

stop means attached to the tubular body and arranged to abut the pin such that the control wheel may be rotated 180 degrees in either direction from a predetermined neutral point;

elongate torque transmitting means extending coincident with the second axis through the passage and attached to the control wheel with the set screw, wherein the torque transmitting means rotates over its entire length when the control wheel is rotated;

rotatable positioning support means attached to the torque means at the distal end; and working means remote from the body attached to the positioning means for rotation therewith.

18. The control handle of claim 17 wherein the tactile ridges are provided with a detente which cooperates with the stop means and wherein the stop means is spring biased to provide a textile feedback of each 45 degrees of rotation for the control wheel.

19. The control handle of claim 18 wherein the detente corresponding to the neutral position is overrideably constructed and arranged to provide stronger tactile feedback to signify rotation of the control wheel substantially 180 degrees in either direction.

20. The control handle of claim 17 wherein the means attached to the positioning means is an optical fiber means.

21. The control handle of claim 17 further including a handle catheter interlock collar carried by the catheter and constructed and arranged to be removably received into an opening in an end cap of the body.

22. A control handle comprising:
a hollow tubular grip portion having front and rear openings and defining a first longitudinal axis;

a rear end cap attached to the rear of the grip and having an opening defining a second longitudinal axis below the first axis and parallel thereto;

a rear control wheel support attached to the front of the grip portion and having another opening correspondingly positioned relative to the opening in the rear end cap and a second opening defining a third longitudinal axis parallel to and above the first axis;

a control wheel enclosure element having front and rear openings and an opening in the top, the enclosure being attached to the rear control wheel support at the rear of the enclosure;

a front control wheel support attached to the front of the enclosure and having two openings correspondingly positioned relative to the two openings in the rear control wheel support, and further including stop means extending into the enclosure element and attached to the front support;

a hollow front tubular piece attached to the front support and having a longitudinal axis coincident with the first axis;

a front end cap attached to the front tubular piece and having a opening coincident with the third longitudinal axis defined by the second opening in the rear control wheel support;

a rotatable control wheel having front and rear axles placed in the openings coincident with the third longitudinal axis in the front and rear control wheel support, the control wheel further including a set of eight tactile ridges spaced 45 degrees from each other around the circumference of the control wheel and extending longitudinally, having a set screw for securing a torque transmitting means and also having a pin which is constructed and arranged to abut the stop means limiting the rotation of the control wheel to 180 degrees in either direction from a predetermined neutral point;

elongated torque transmitting means having proximal and distal ends extending coincident to the third axis through the opening in the front end cap and attached to the control wheel with the set screw, wherein the torque transmitting means rotates over its entire length when the control wheel is rotated; rotatable positioning support means attached to the torque transmitting means at the distal end for rotation therewith, and working means remote from the body attached to the positioning support means for rotation therewith.

* * * * *

UNITED STATES PATENT AND TRADEMARK OFFICE
CERTIFICATE OF CORRECTION

PATENT NO. : 4,874,371

DATED : October 17, 1989

INVENTOR(S) : RICHARD H. COMBEN, ET AL

It is certified that error appears in the above-identified patent and that said Letters Patent is hereby corrected as shown below:

Col. 3, line 62, delete "materil" and insert therefore -- material --

Col. 6, line 44, delete "Th" and insert therefore -- The --

Signed and Sealed this

Thirty-first Day of December, 1991

Attest:

HARRY F. MANBECK, JR.

Attesting Officer

Commissioner of Patents and Trademarks